(12) United States Patent
Chen et al.

(10) Patent No.: US 12,263,297 B2
(45) Date of Patent: Apr. 1, 2025

(54) QUICK-RELEASE NEBULIZER

(71) Applicant: GALEMED CORPORATION, Yilan County (TW)

(72) Inventors: Po-Chang Chen, Yilan County (TW); Hsin-Chen Wang, Yilan County (TW); Chia-Chin Yang, Yilan County (TW); Hao-Hsiang Chen, Yilan County (TW); Chun-Wei Hsu, Yilan County (TW)

(73) Assignee: GALEMED CORPORATION, Yilan County (TW)

( * ) Notice: Subject to any disclaimer, the term of this patent is extended or adjusted under 35 U.S.C. 154(b) by 574 days.

(21) Appl. No.: 17/826,142

(22) Filed: May 26, 2022

(65) Prior Publication Data

US 2023/0405244 A1    Dec. 21, 2023

(51) Int. Cl.
*A61M 15/00*    (2006.01)

(52) U.S. Cl.
CPC ..... *A61M 15/0001* (2014.02); *A61M 2205/11* (2013.01); *A61M 2207/10* (2013.01)

(58) Field of Classification Search
CPC .............. A61M 11/00–08; A61M 15/00–085
See application file for complete search history.

(56) References Cited

U.S. PATENT DOCUMENTS

| | | | |
|---|---|---|---|
| 2008/0029085 A1* | 2/2008 | Lawrence | A61M 15/0081 116/284 |
| 2013/0327323 A1* | 12/2013 | Rubin | A61M 16/1065 128/200.14 |
| 2021/0113784 A1* | 4/2021 | Kolb | B05B 15/55 |

* cited by examiner

*Primary Examiner* — Rachel T Sippel
(74) *Attorney, Agent, or Firm* — Chun-Ming Shih; HDLS IPR SERVICES (57) ABSTRACT

A nebulizer includes a main body (1), a spraying head (2) and an engagement structure (4). The main body (1) includes a body (11). The spraying head (2) includes a spraying seat (21) assembled to the body (11). The engagement structure (4) includes a notch (41) formed on one of the body (11) and the spraying seat (21), a T-shaped trench (42) formed on an inner wall of the notch (41), an engaging trench (43) formed on another one of the body (11) and the spraying seat (21), and a movable member (44) received in the notch (41). The movable member (44) is extended with a handle (441) exposed from the notch (41), a T-shaped block (442) slidably received in the T-shaped trench (42) and an engaging block (443) embedded in or separated from the engaging trench (43).

10 Claims, 10 Drawing Sheets

QUICK-RELEASE NEBULIZER

BACKGROUND

Technical Field

The disclosure relates to a nebulizer structure, particularly to a quick-release nebulizer.

Description of Related Art

A related-art nebulizer usually uses compressed gas supplied by a gas supply to nebulize an agent, and then the nebulized agent is driven by the compressed gas to be ejected for being sucked by a patient so that the nebulized agent can be diffused to the patient's lung though his or her bronchus.

However, after such a nebulizer has been used, its spraying head must be removed and washed to prevent contagious germs from spreading through the respiratory organs. Thus, how to conveniently and rapidly install and remove a spraying head becomes an issue to be researched.

In view of this, the inventors have devoted themselves to the above-mentioned related art, researched intensively and cooperated with the application of science to try to solve the above-mentioned problems. Finally, the invention which is reasonable and effective to overcome the above drawbacks is provided.

SUMMARY

An object of the disclosure is to provide a quick-release nebulizer, which utilizes the spraying seat being assembled to or disassembled from the body along the radial direction and the movable member being pushed along the axial direction to make the engaging block be embedded in or separated from the engaging trench so as to rapidly install or remove the spraying head.

In an embodiment of the disclosure, the disclosure provides a quick-release nebulizer, which includes a main body, a spraying head, and an engagement structure. The main body includes a body. The body defines an axial direction and a radial direction. The spraying head includes a spraying seat assembled to or disassembled from the body along the radial direction. The engagement structure includes a notch formed on one of the body and the spraying seat, a T-shaped trench formed on an inner wall of the notch along the axial direction, an engaging trench formed on another one of the body and the spraying seat and arranged corresponding to the notch, and a movable member received in the notch. A side of the movable member is extended with a handle exposed from the notch, another side thereof is extended with a T-shaped block slidably received in the T-shaped trench, and still another side thereof is protruded with an engaging block embedded in or separated from the engaging trench.

Accordingly, the spraying seat is assembled to the body through the sliding rail structure along the radial direction, and then the handle is pushed upward along the axial direction to drive the whole movable member to move upward to make the engaging block be embedded in the engaging trench to lock the spraying seat. As a result, the spraying head may be rapidly assembled to the main body. On the contrary, the handle is pushed downward along the axial direction to drive the whole movable member to move downward to make the engaging block disengage from the engaging trench to release the spraying seat, and then the spraying seat is removed from the body through the sliding rail structure along the radial direction. As a result, the spraying head may be rapidly disassembled to the main body. Therefore, the quick-release nebulizer has the function of conveniently and rapidly assembling and disassembling the spraying head.

DETAILED DESCRIPTION

The technical contents of this disclosure will become apparent with the detailed description of embodiments accompanied with the illustration of related drawings as follows. It is intended that the embodiments and drawings disclosed herein are to be considered illustrative rather than restrictive.

Figure 1:
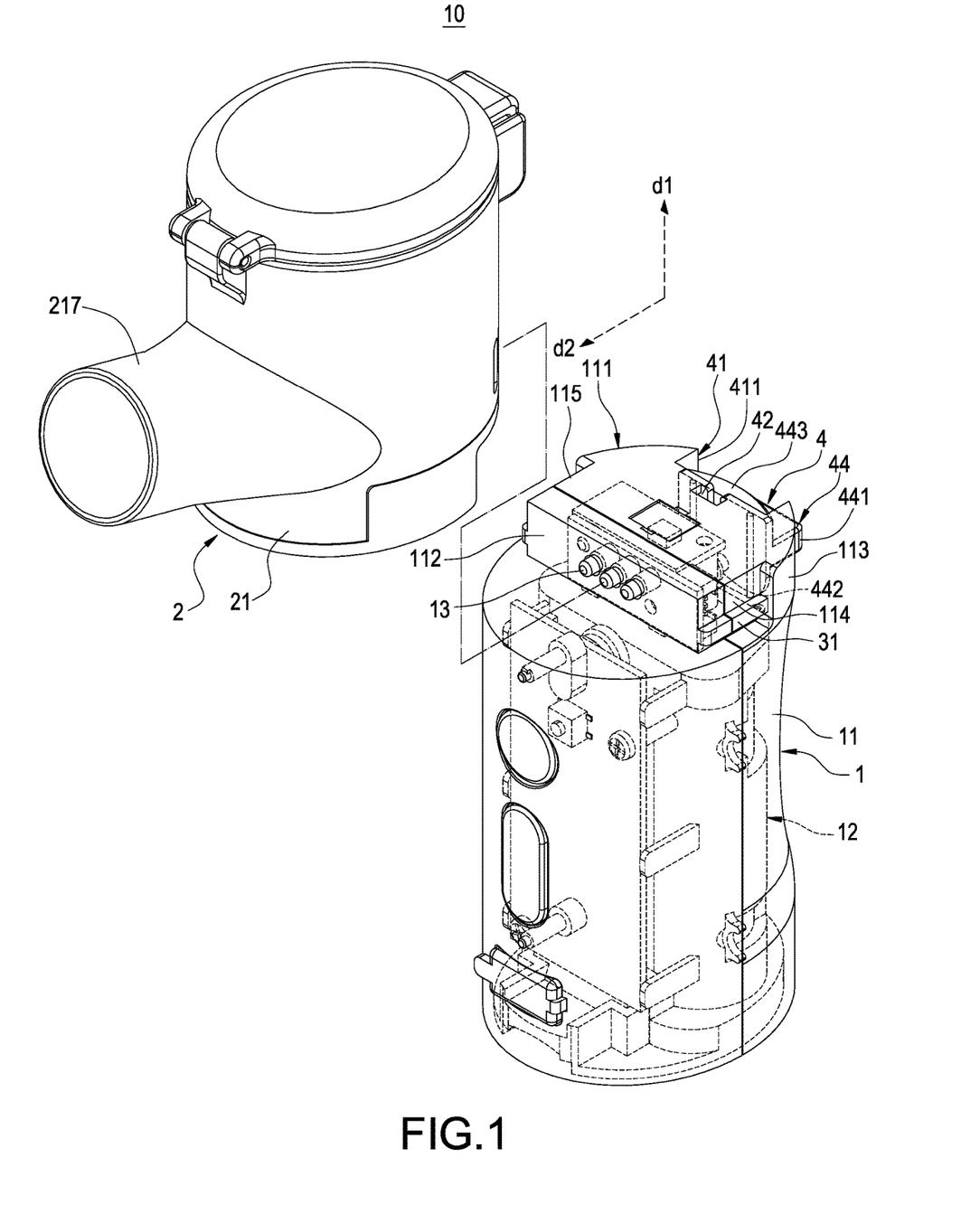
FIG. 1 is an exploded view of the quick-release nebulizer of the disclosure.
Figure 2:
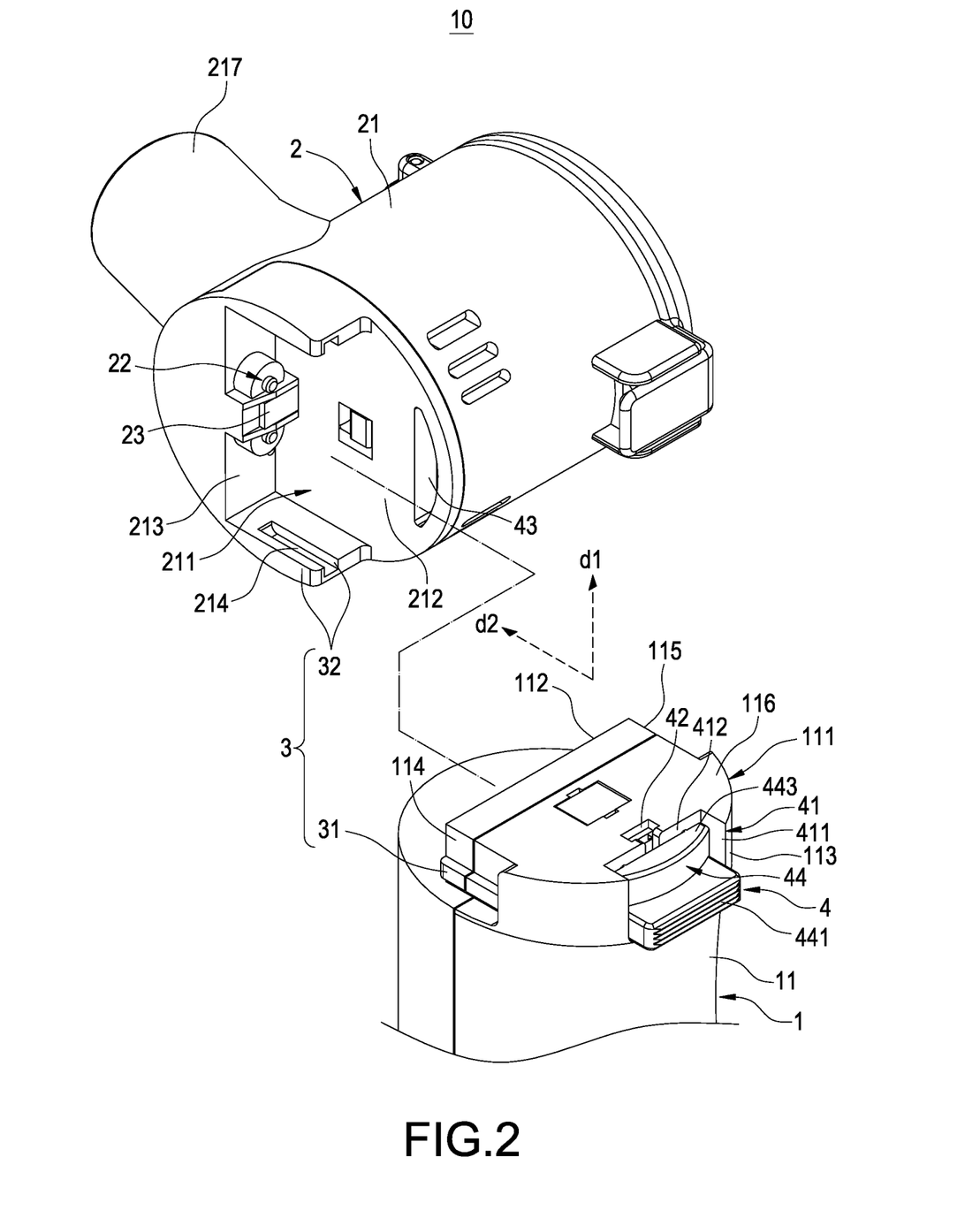
FIG. 2 is another exploded view of the quick-release nebulizer of the disclosure.
Figure 3:
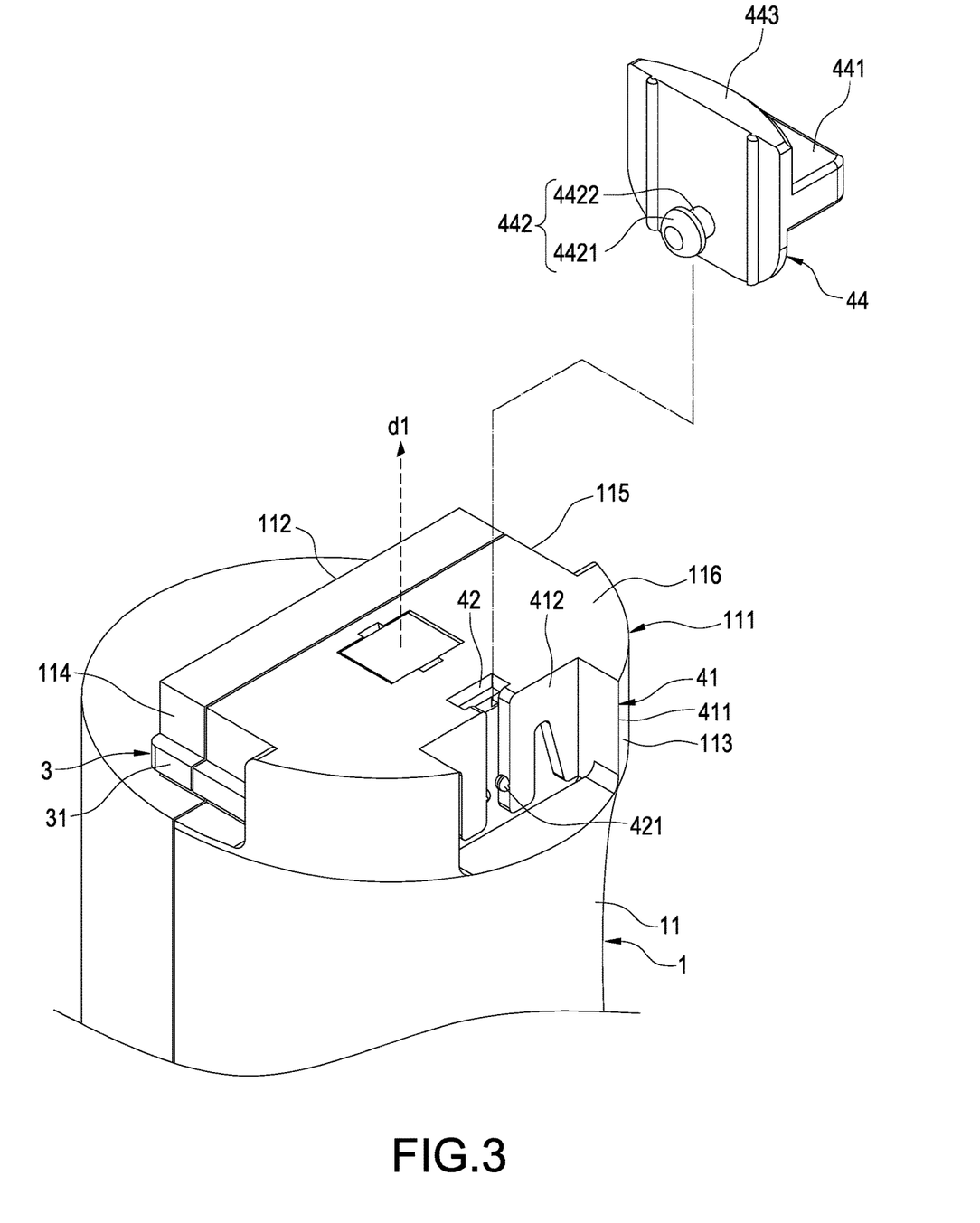
FIG. 3 is still another exploded view of the quick-release nebulizer of the disclosure.
Figure 4:
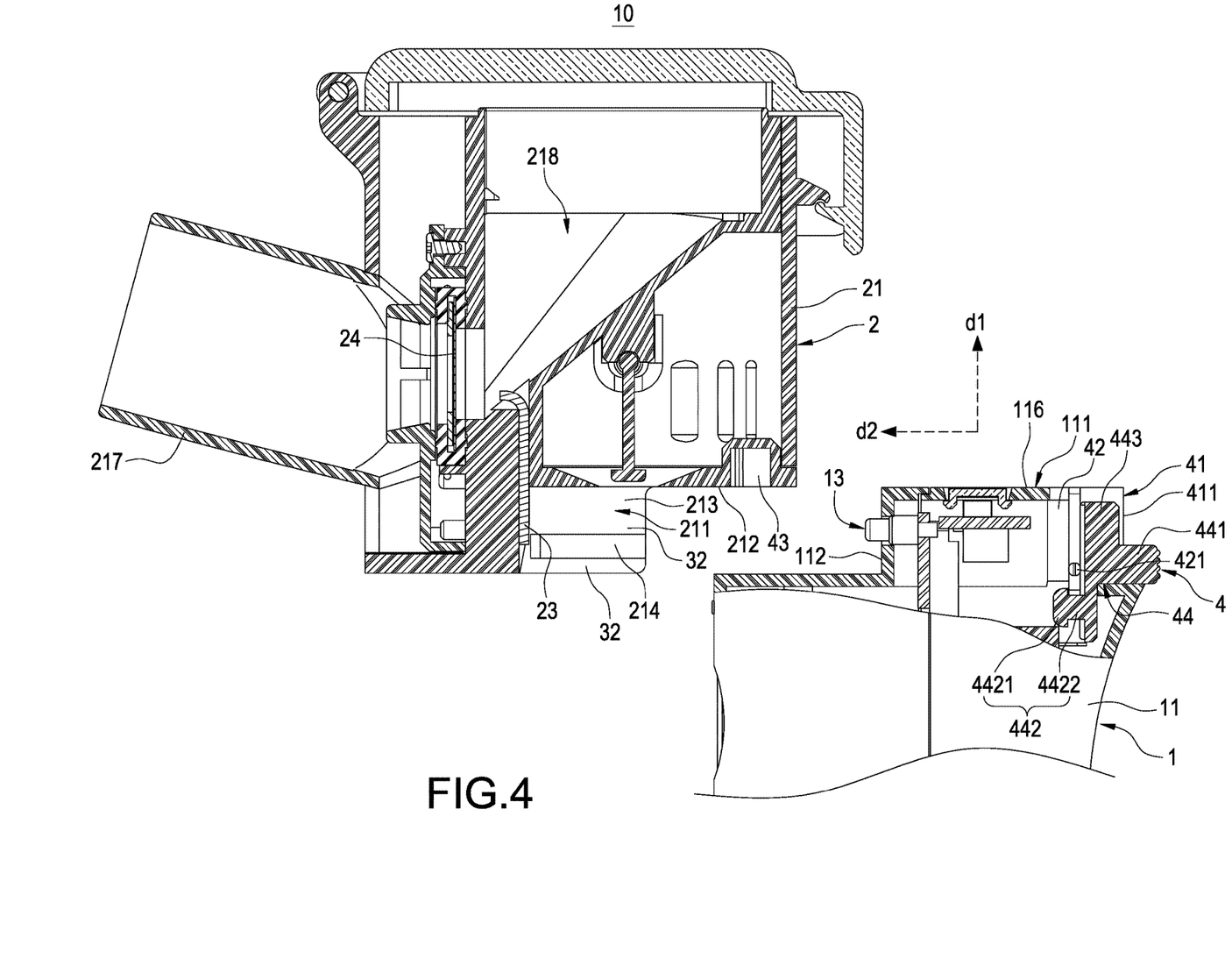
FIG. 4 is an exploded cross-sectional view of the quick-release nebulizer of the disclosure.
Figure 5:
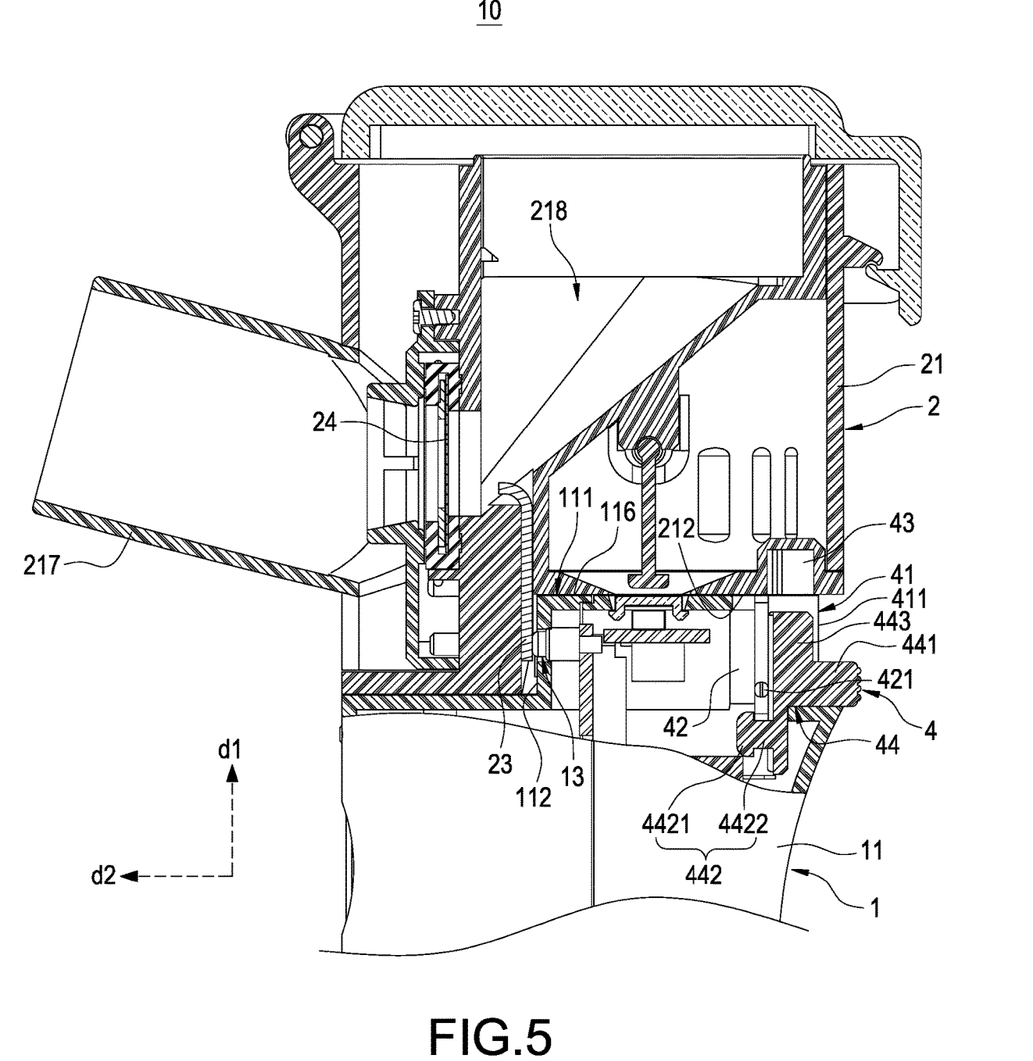
FIG. 5 is the first assembled cross-sectional view of the quick-release nebulizer of the disclosure.
Figure 6:
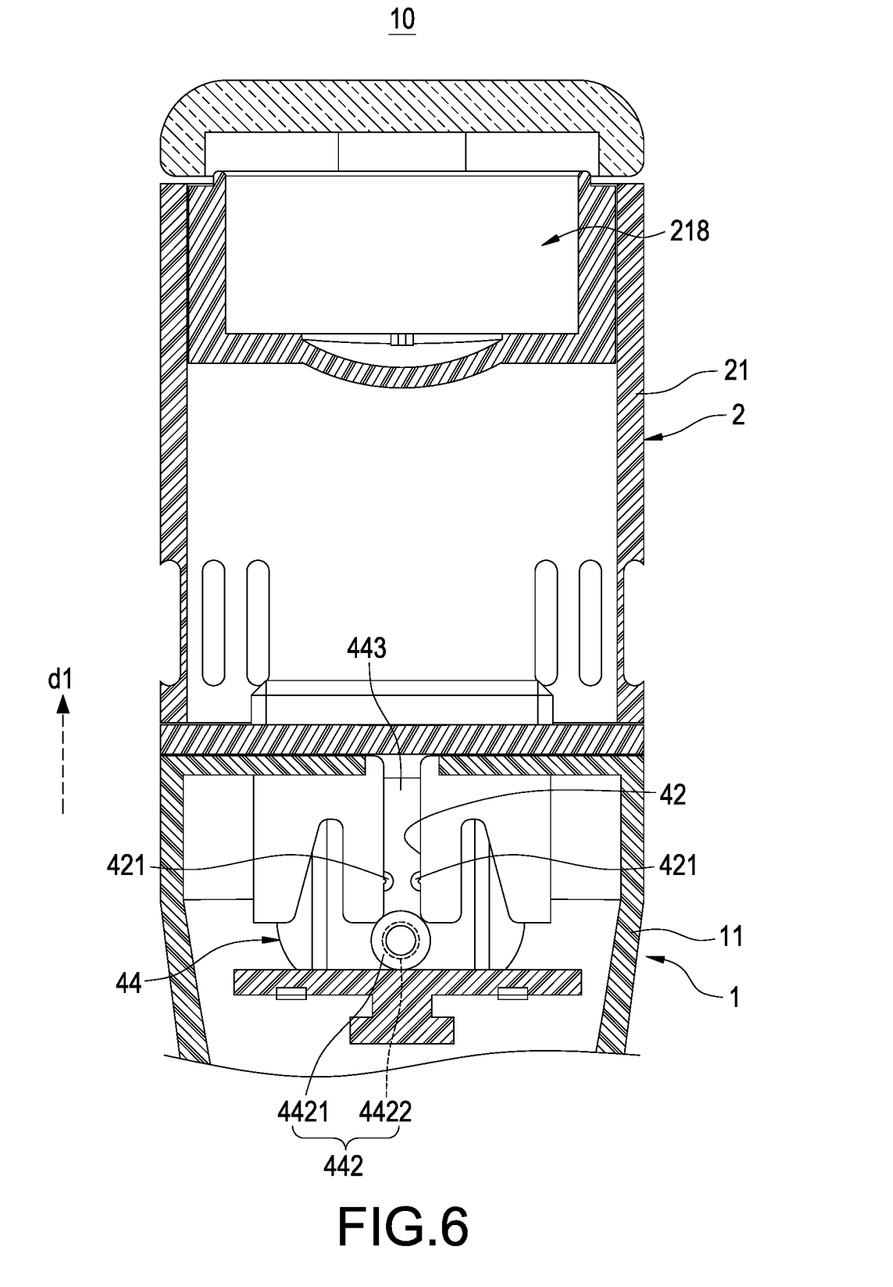
FIG. 6 is the second assembled cross-sectional view of the quick-release nebulizer of the disclosure.
Figure 7:
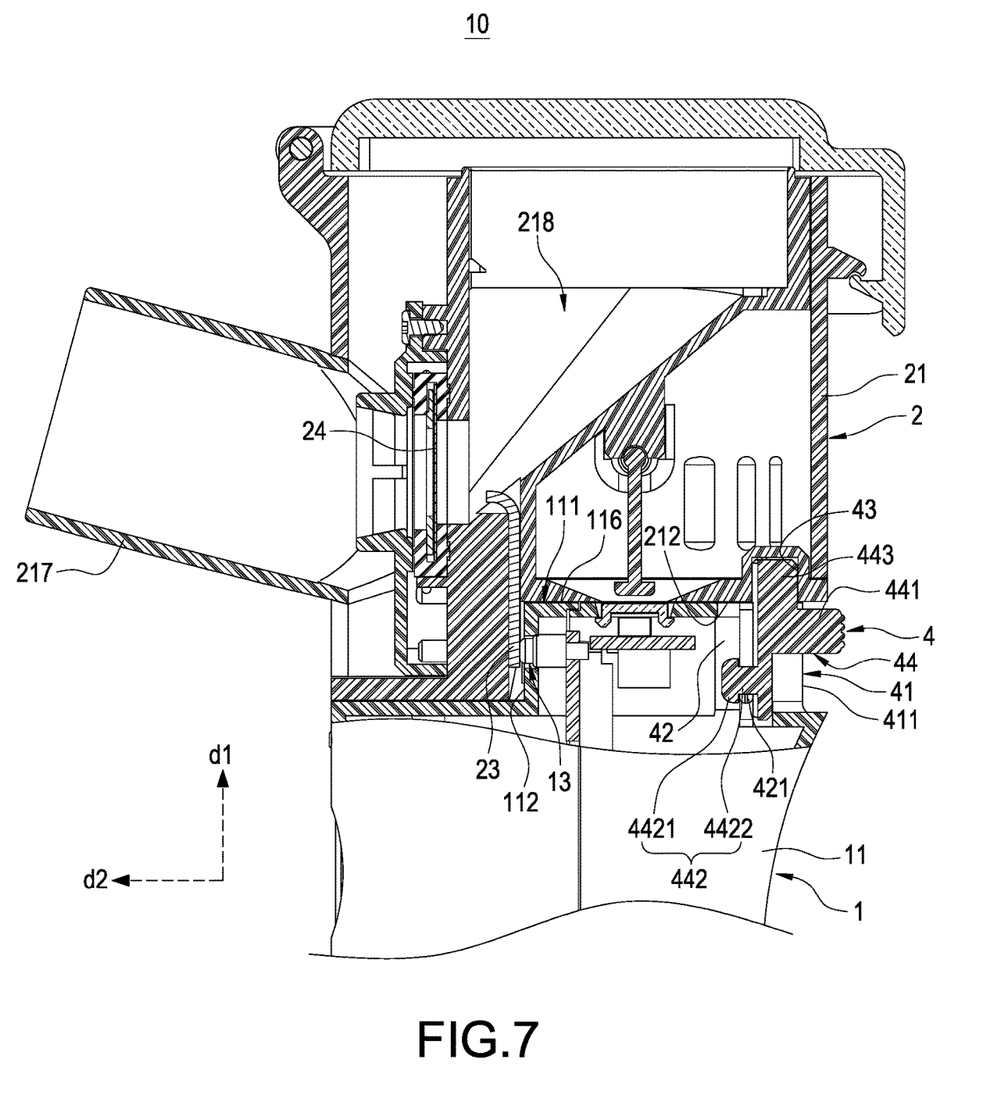
FIG. 7 is the third assembled cross-sectional view of the quick-release nebulizer of the disclosure.
Figure 8:
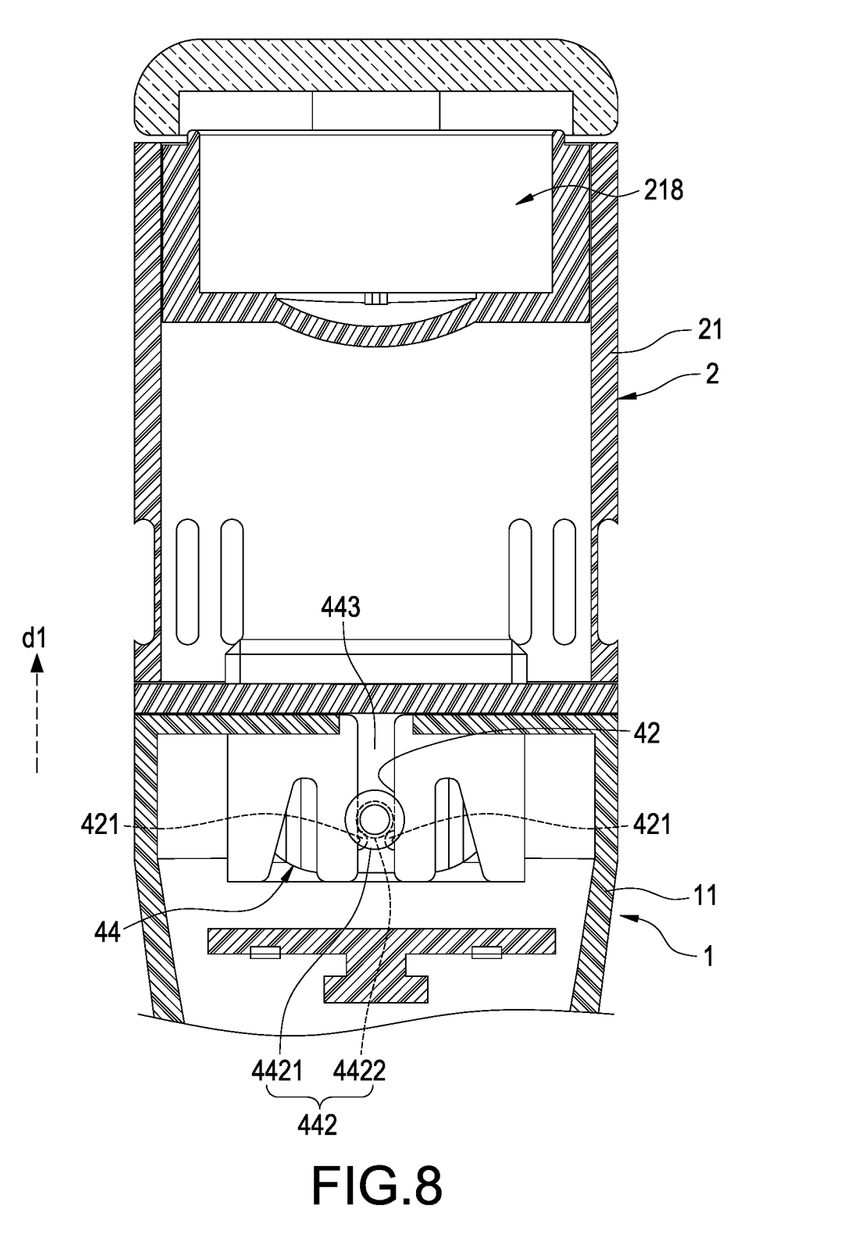
FIG. 8 is the fourth assembled cross-sectional view of the quick-release nebulizer of the disclosure.
Figure 9:
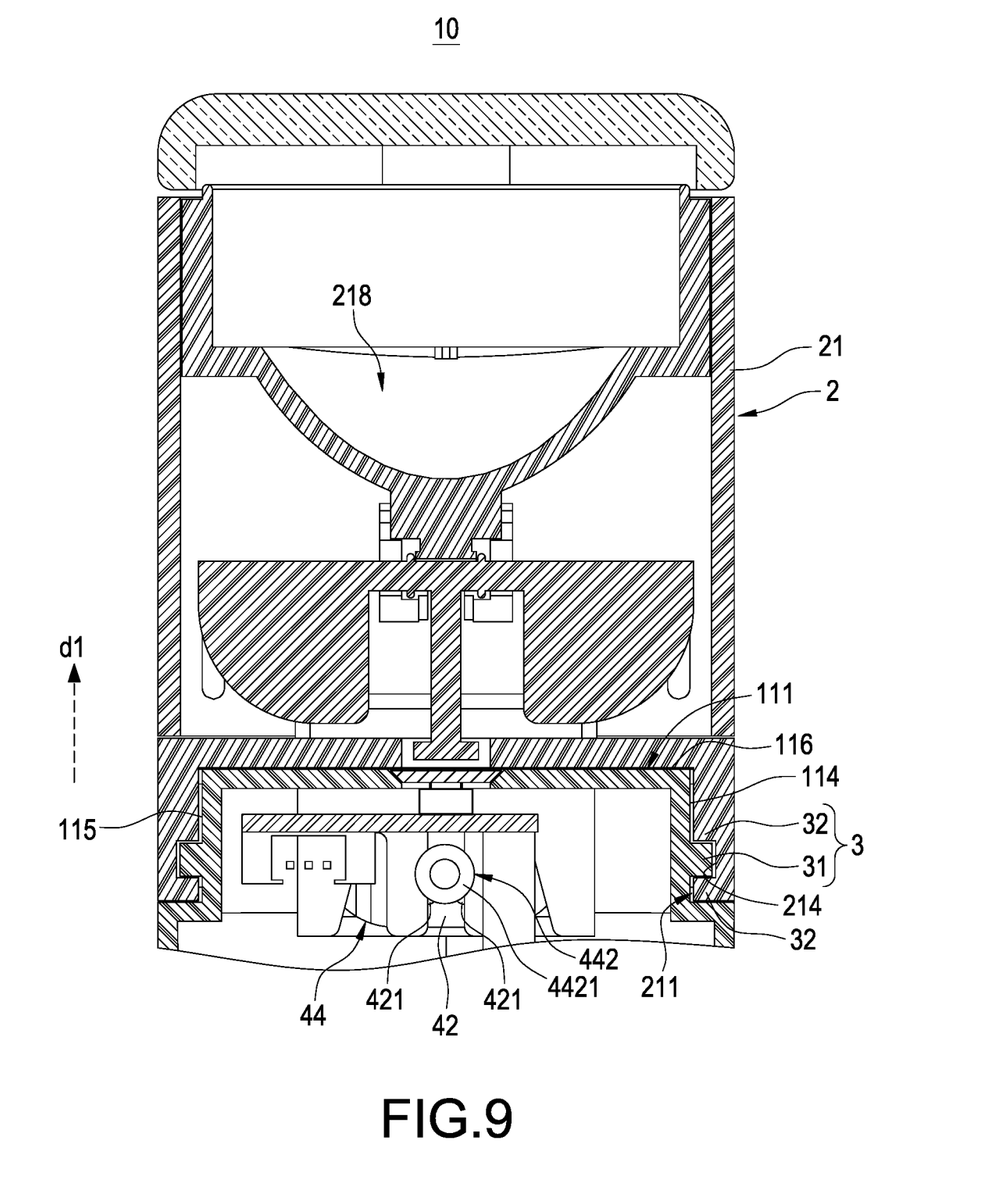
FIG. 9 is the fifth assembled cross-sectional view of the quick-release nebulizer of the disclosure.
Figure 10:
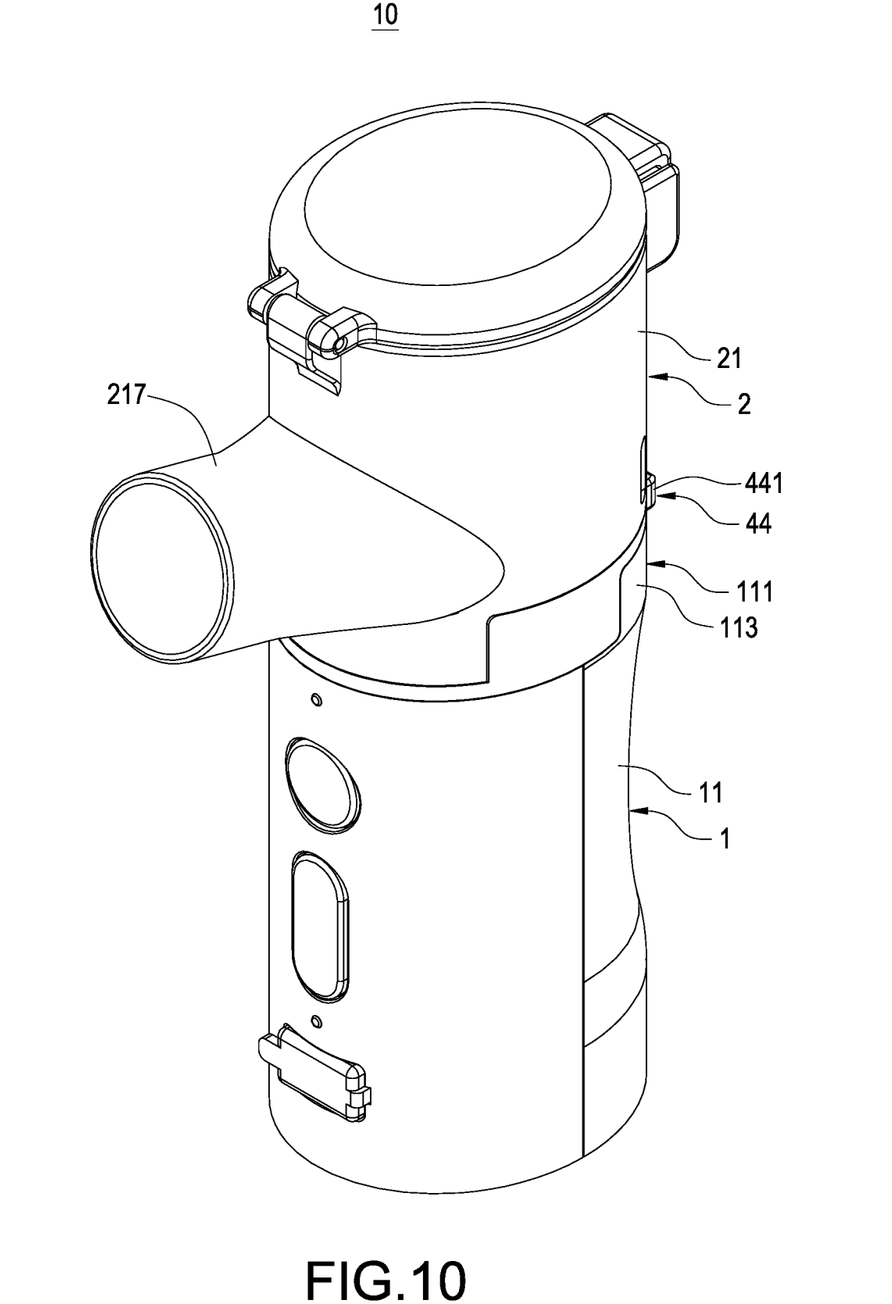
FIG. 10 is a perspective assembled view of the quick-release nebulizer of the disclosure.

Please refer to FIGS. 1-10. The disclosure provides a quick-release nebulizer. The nebulizer 10 includes a main body 1, a spraying head 2 and an engagement structure 4.

As shown in FIGS. 1-10, the main body 1 includes a body 11, a power assembly 12 received in the body 11 and a first conductive member 13 electrically connected to the power assembly 12. The body 11 defines an axial direction d1 and a radial direction d2. In the embodiment, the power assembly 12 includes a circuit board and a battery, and the first conductive member 13 includes multiple pogo pins, but not limited to these.

In addition, the top of the body 11 is protruded with a block 111. The block 111 has a front side 112, a rear side 113, a left side 114, a right side 115 and a top side 116. The first conductive member 13 is installed on the front side 112.

As shown in FIGS. 1, 2 and 4-10, the spraying head 2 includes a spraying seat 21 assembled to (assemblable with) or disassembled from (detachable with) the body 11 along the radial direction d2. The bottom and the outer periphery of the spraying seat 21 are formed with a recess 211. The recess 211 has an inner bottom 212 and a U-shaped inner sidewall 213 disposed on a side of the inner bottom 212.

In detail, as shown in FIGS. 1-3 and 9, the quick-release nebulizer 10 of the disclosure further includes a sliding rail structure 3. The sliding rail structure 3 includes one or more sliders 31 formed on either one of the body 11 and the spraying seat 21 and one or multiple pairs of rails 32 formed on the other one of the body 11 and the spraying seat 21.

In the embodiment, the sliders 31 are two in number, and the rails 32 are two pairs in number, but not limited to these. The two sliders 31 are formed by protruding from the left side 114 and the right side 115 of the block 111. Two sides of the U-shaped inner sidewall 213 are formed with two rail grooves 214 along the radial direction d2. The U-shaped inner sidewall 213 is formed with each pair of rails 32 corresponding to the upper side and the lower side of each rail groove 214 so that each pair of rails 32 is arranged along the radial direction d2 and in a top-and-bottom configuration. Each slider 31 is slidable and stopped between each pair of rails 32 so as to make the spraying seat 21 be able to be assembled to or disassembled from the body 11 along the radial direction d2.

In addition, the spraying head 2 further includes a second conductive member 22 and a no-water detection probe 23. The second conductive member 22 is installed on the U-shaped inner sidewall 213 and abuts against the first conductive member 13. The power assembly 12 transmits electricity to the no-water detection probe 23 only via the first conductive member 13. The second conductive member 22 in the embodiment includes, but not limited to, multiple conductive terminals.

Also, the outside of the spraying seat 21 is extended with a nozzle 217 and the inside thereof is disposed with an agent chamber 218 communicating with the nozzle 217. The spraying head 2 further includes a nebulizing sheet 24 installed at the junction between the nozzle 217 and the agent chamber 218. An end of the no-water detection probe 23 stretches in the agent chamber 218 and is arranged corresponding to the nebulizing sheet 24. The nebulizing sheet 24 is electrically connected with the second conductive member 22. The power assembly 12 transmits electricity to the nebulizing sheet 24 via the first conductive member 13 and the second conductive member 22. The no-water detection probe 23 is used to detect if liquid exists after being electrified. The nebulizing sheet 24 vibrates after being electrified to nebulize liquid in the agent chamber 218 and allows the nebulized liquid to pass through for being ejected through the nozzle 217.

As shown in FIGS. 1-10, the engagement structure 4 includes a notch 41 formed on one of the body 11 and the spraying seat 21, a T-shaped trench 42 formed on an inner wall of the notch 41 along the axial direction d1, an engaging trench 43 formed on the other one of the body 11 and the spraying seat 21 and arranged corresponding to the notch 41, and a movable member 44 movably received in the notch 41.

In addition, a side of the movable member 44 is extended with a handle 441 exposed from the notch 41, another side thereof is extended with a T-shaped block 442 slidably received in the T-shaped trench 42, and still another side thereof is protruded with an engaging block 443 along the axial direction d1, which may be embedded in or separated from the engaging trench 43.

Further, the T-shaped block 442 has a head portion 4421 and a rod portion 4422 connected between the head portion 4421 and the movable member 44. The inner wall of the T-shaped trench 42 is extended with two resistant bumps 421 that are frictional with the rod portion 4422.

Also, the notch 41 of the embodiment is formed by indenting the rear side 113 and the top side 116. The notch 41 has an opening 411 formed on the rear side 113 and an inner end face 412 corresponding to the opening 411. The T-shaped trench 42 is formed by indenting the inner end face 412 and the top side 116. The engaging trench 43 is formed by indenting the inner bottom 212. The handle 441 is exposed from the opening 411.

In detail, when the engaging block 443 is embedded in the engaging trench 43, the rod portion 4422 goes up over the two resistant bumps 421 and rubs the two resistant bumps 421 to transmit a hand-operated resistance. After that, the two resistant bumps 421 abut against the bottom edge of the rod portion 4422 to temporarily lock the position of the movable member 44 until a user downward pushes the handle 441 to move the rod portion 4422 to go down over the two resistant bumps 421 so as to release the position of the movable member 44 to make the engaging block 443 smoothly disengage from the engaging trench 43.

As shown in FIGS. 1-10, when using the quick-release nebulizer 10 of the disclosure, the spraying seat 21 is assembled to the body 11 through the sliding rail structure 3 along the radial direction d2 first, and then the handle 441 is pushed upward along the axial direction d1 to drive the whole movable member 44 to move upward so as to make the engaging block 443 be embedded in the engaging trench 43 to lock the spraying seat 21. As a result, the spraying head 2 may be rapidly assembled to the main body 1. On the contrary, the handle 441 is pushed downward along the axial direction d1 to drive the whole movable member 44 to move downward so as to make the engaging block 443 disengage from the engaging trench 43 to release the spraying seat 21, and then the spraying seat 21 is removed from the body 11 through the sliding rail structure 3 along the radial direction d2. As a result, the spraying head 2 may be rapidly disassembled from the main body 1. Therefore, the quick-release nebulizer has the function of conveniently and rapidly assembling and disassembling the spraying head 2.

While this disclosure has been described by means of specific embodiments, numerous modifications and variations could be made thereto by those skilled in the art without departing from the scope and spirit of this disclosure set forth in the claims.

What is claimed is:

1. A nebulizer comprising:
a main body (1), comprising a body (11), and the body (11) defining an axial direction (d1) and a radial direction (d2);
a spraying head (2), comprising a spraying seat (21) assembled to or disassembled from the body (11) along the radial direction (d2); and
an engagement structure (4), comprising a notch (41) disposed on one of the body (11) and the spraying seat (21), a T-shaped trench (42) disposed on an inner wall of the notch (41) along the axial direction (d1), an engaging trench (43) disposed on another one of the body (11) and the spraying seat (21) and arranged corresponding to the notch (41), and a movable member (44) received in the notch (41), wherein a side of the movable member (44) is extended with a handle (441) exposed from the notch (41), another side of the movable member (44) is extended with a T-shaped block (442) slidably received in the T-shaped trench (42), and still another side of the movable member (44) is protruded with an engaging block (443) embedded in or separated from the engaging trench (43) along the axial direction.

2. The nebulizer of claim 1, wherein the T-shaped block (442) comprises a head portion (4421) and a rod portion (4422) connected between the head portion (4421) and the movable member (44), and an inner wall of the T-shaped trench (42) is extended with two resistant bumps (421) being frictional with the rod portion (4422).

3. The nebulizer of claim 2, further comprising a sliding rail structure (3), wherein the sliding rail structure (3)

comprises at least one slider (31) disposed on either one of the body (11) and the spraying seat (21) and at least one pair of rails (32) disposed on another one of the body (11) and the spraying seat (21), the at least one pair of rails (32) is arranged along the radial direction (d2) and in a top-and-bottom configuration, and the at least one slider (31) is slidable and stopped between the at least one pair of rails (32).

4. The nebulizer of claim 3, wherein a top of the body (11) is protruded with a block (111), the block (111) comprises a rear side (113), a left side (114), a right side (115) and a top side (116), the slider (31) is two in number, the two sliders (31) protrude from the left side (114) and the right side (115), and the notch (41) is indented on the rear side (113) and the top side (116).

5. The nebulizer of claim 4, wherein the notch (41) comprises an opening (411) defined on the rear side (113) and an inner end face (412) corresponding to the opening (411), the T-shaped trench (42) is indented on the inner end face (412) and the top side (116), and the handle (441) is exposed from the opening (411).

6. The nebulizer of claim 4, wherein a bottom and an outer periphery of the spraying seat (21) are disposed with a recess (211), the recess (211) comprises an inner bottom (212) and a U-shaped inner sidewall (213) disposed on a side of the inner bottom (212), the engaging trench (43) is indented on the inner bottom (212), and the two resistant bumps (421) abut against a bottom edge of the rod portion (4422) when the engaging block (443) is embedded in the engaging trench (43).

7. The nebulizer of claim 6, wherein the rails (32) are two pairs in number, two sides of the U-shaped inner sidewall (213) are disposed with two rail grooves (214) along the radial direction (d2), and each pair of rails (32) is disposed on an upper side and a lower side of each rail groove (214) correspondingly.

8. The nebulizer of claim 6, wherein the block (111) comprises a front side (112), the main body (1) comprises a power assembly (12) received in the body (11) and a first conductive member (13) installed on the front side (112) and electrically connected to the power assembly (12).

9. The nebulizer of claim 8, wherein an outside of the spraying seat (21) is extended with a nozzle (217) and an inside of the spraying seat (21) is disposed with an agent chamber (218) communicating with the nozzle (217), and the spraying head (2) further comprises a nebulizing sheet (24) installed at a junction between the nozzle (217) and the agent chamber (218).

10. The nebulizer of claim 9, wherein the spraying head (2) further comprises a second conductive member (22) and a no-water detection probe (23), the second conductive member (22) is installed on the U-shaped inner sidewall (213) and abuts against the first conductive member (13), an end of the no-water detection probe (23) stretches in the agent chamber (218) and is arranged corresponding to the nebulizing sheet (24), and the nebulizing sheet (24) is electrically connected with the second conductive member (22).

* * * * *